United States Patent [19]

Kanazawa et al.

[11] 4,084,061
[45] Apr. 11, 1978

[54] PROCESS FOR PRODUCING BENZYL SODIUM, PHENYLACETIC ACID AND DERIVATIVE THEREOF

[75] Inventors: Teiichi Kanazawa, Shimizu; Masamichi Shimizu, Kashiwa; Susumu Shimoyama, Tokyo, all of Japan

[73] Assignee: Ihara Chemical Industry Co., Ltd., Tokyo, Japan

[21] Appl. No.: 708,648

[22] Filed: Jul. 26, 1976

[30] Foreign Application Priority Data

Jul. 30, 1975 Japan .................................. 50-92760

[51] Int. Cl.$^2$ ........................ C07C 63/04; C07C 69/76
[52] U.S. Cl. ................................ 560/105; 260/515 R; 260/665 R
[58] Field of Search ............ 260/476 R, 665 R, 515 R

[56] References Cited

U.S. PATENT DOCUMENTS 2,881,209  4/1959  Nobis et al. ....................... 260/476 R
3,346,634  10/1967  Christensen et al. ............. 260/665 R

OTHER PUBLICATIONS

Patai, The Chemistry of Carboxylic Acids and Esters, pp. 146–148 (1969).

Primary Examiner—Jane S. Myers
Attorney, Agent, or Firm—Oblon, Fisher, Spivak, McClelland & Maier

[57] ABSTRACT

Phenylacetic acid is produced by reacting chlorotoluene with sodium to form tolylsodium, rearranging the product to benzyl sodium and then reacting the benzyl sodium with a carboxylating agent.

12 Claims, No Drawings

PROCESS FOR PRODUCING BENZYL SODIUM, PHENYLACETIC ACID AND DERIVATIVE THEREOF

BACKGROUND OF THE INVENTION

1. Field of the Invention

The present invention relates to a process for producing benzylsodium as an intermediate for the production of phenylacetic acid and derivatives thereof.

The present invention also relates to a process for producing phenylacetic acid, salts or esters thereof which are useful as precursors for the synthesis of penicillin G, perfume additives and as intermediates for dyes, medicines, agricultural chemicals and the like. More particularly, it relates to a process for producing phenylacetic acid, salts or esters thereof in high yield from chlorotoluene as a starting material and by a previously unknown rearrangement. Heretofore, phenylacetic acid has been produced by reacting chlorobenzene with sodium at a temperature less than 40° C to yield phenylsodium, and then reacting toluene with phenylsodium to yield benzylsodium and reacting carbon dioxide with the benzylsodium to yield sodium phenylacetate. The sodium phenylacetate is then contacted with a mineral acid to yield phenylacetic acid as shown in the following reaction sequence. (Industrial and Engineering Chemistry 46, Page 539, 1954).

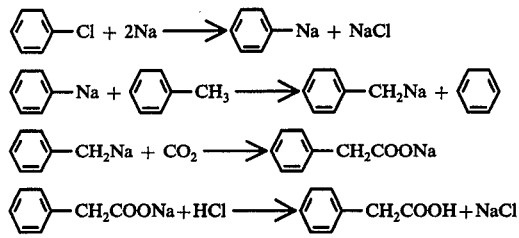

However, the reaction temperature of the conventional procedure which uses the chlorobenzene as the starting material, is hard to control in the step in which chlorobenzene is reacted with sodium. The difficulty in controlling the temperature makes it difficult to control the formation of biphenyl by-product. In other words, the reaction between chlorobenzene and sodium is not smooth at temperatures less than 30° C. If the temperature is higher than 40° C, a side reaction occurs between phenyl sodium and the chlorobenzene starting material which produces biphenyl as follows.

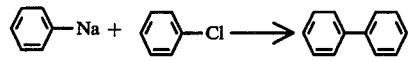

Thus, in order to inhibit the formation of the by-product biphenyl, it is necessary to control the reaction temperature in a range of 31° C to 40° C.

The reaction of chlorobenzene with sodium is a severe exothermic reaction, and consequently, it is hard to control the reaction temperature and prevent the formation of by-product biphenyl. Moreover, the conventional method of using chlorobenzene has the disadvantage in that large amounts of by-product benzene are formed. In the process, phenylsodium obtained by the reaction of chlorobenzene with sodium is reacted with toluene to yield benzylsodium. In the reaction of phenylsodium with toluene, benzene is necessarily formed as a coproduct with benzylsodium. Thus, benzene is unavoidably formed as a by-product in the conventional process.

A need, therefore, continues to exist for a method by which benzylsodium can be prepared as an intermediate for the synthesis of phenylacetic acid.

SUMMARY OF THE INVENTION

Accordingly, one object of the present invention is to provide a process for producing benzyl sodium as an intermediate for the synthesis of phenylacetic acid and derivatives thereof.

Another object of the present invention is to provide a process for producing phenylacetic acid, salts or esters thereof in high yield without the above-described disadvantages.

Yet another object of the invention is to produce phenylacetic acid, salts or esters thereof by using chlorotoluene which is an industrial waste as a starting material.

Briefly, these and other objects of the present invention as hereinafter will become more readily apparent can be attained by preparing phenylacetic acid, salts or esters thereof by reacting chlorotoluene with sodium, rearranging the resultant tolyl sodium to benzylsodium and then reacting a carboxylating agent such as carbon dioxide or an alkyl chloroformate with said benzylsodium. The sodium salt or ester of phenylacetic acid obtained by this method can be converted to phenylacetic acid by reacting it with a mineral acid or by hydrolysis. If dichlorotoluene is used, it is possible to obtain chlorophenylacetic acid, salts or esters thereof as a product when reacted with sodium.

DETAILED DESCRIPTION OF THE PREFERRED EMBODIMENTS

An object of the study behind the present invention has been to produce phenylacetic acid in high yield without the disadvantages of the conventional procedure. As a result, it has been found that the reaction of chlorotoluene with sodium occurs smoothly at low temperature to produce tolylsodium, which readily undergoes rearrangement to benzyl sodium. The following findings reside behind the present invention. As shown by the following reaction sequence, the first embodiment of the invention shows the production of phenylacetic acid by reacting chlorotoluene with sodium rearranging the resulting tolyl sodium to benzyl sodium and then reacting the benzylsodium with carbon dioxide and reacting the product with a mineral acid. In the second embodiment of the invention, an alkyl phenylacetate is prepared by reacting chlorotoluene with sodium, rearranging the resulting tolylsodium to benzyl sodium and then reacting an alkyl chloroformate with the benzylsodium.

FIRST EMBODIMENT

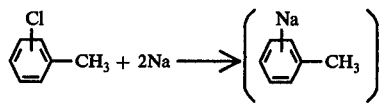

-continued

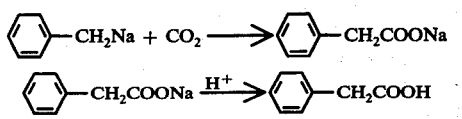

SECOND EMBODIMENT

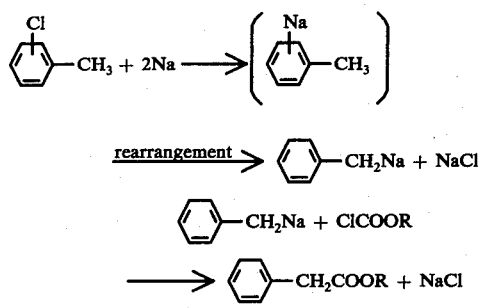

In the second embodiment of the invention, R represents a lower alkyl group of 1 to 4 carbon atoms.

In all embodiments of the invention, when dichlorotoluene is used as the chlorotoluene starting material, chlorotolylsodium is formed and the product rearranges to form chlorobenzylsodium and the product is converted to chlorophenylacetic acid, salts or esters thereof by reacting the product with carbon dioxide, an alkyl chloroformate or the like.

In the preferred embodiments of the present invention, chlorotoluene is contacted with sodium which is dispersed in an inert organic solvent at 0° C to 50° C, preferably 10° C to 40° C for 5 minutes to 2 hours preferably about 30 minutes to 1 hour. Thereafter, rearrangement of the tolylsodium to benzylsodium is accomplished by heating the reaction mixture to 40° C to 150° C, preferably 50° C to 120° C for 1 hour to 10 hours preferably 3 hours to 7 hours. After the rearrangement reacting, carbon dioxide gas is introduced into the reaction mixture at room temperature or solid carbon oxide is added to the reaction mixture at room temperature and then the reaction is conducted to produce sodium phenylacetate. Thereafter, a mineral acid is added to the reaction mixture to produce phenylacetic acid; as shown in the first embodiment.

As shown in the second embodiment, the desired alkyl phenylacetic ester after the rearrangement reaction, is obtained by reacting an alkyl chloroformate with the rearrangement product at 0° C to 50° C preferably 10° C to 30° C. Suitable chloroaromatic starting materials used in the process of the present invention include o-chlorotoluene, m-chlorotoluene, p-chlorotoluene; dichlorotoluene and mixtures thereof. For example, a mixture of o-chlorotoluene, p-chlorotoluene and m-chlorotoluene which is obtained by chlorination of toluene can be a starting material without separation. Suitable inert organic solvents in which sodium can be dispersed include hydrocarbon solvents such as n-hexane, isohexane, heptane, cyclohexane, petroleum ether ligroin, benzene and ether type solvents such as isopropyl ether, butyl ether, tetrahydrofuran, dioxane and the like. The amount of sodium reacted with chlorotoluene is greater than the stoichiometric amount and can be used in largely excessive amounts though it is not economical to do so. Usually, a molar ratio of 1 to 5 of sodium to chlorotoluene is employed. The amount of inert organic solvent used is enough to disperse the sodium and can be used in excess. The amount of the inert organic solvent employed is 0.2 to 50 times preferably 0.5 to 20 times, especially 1 to 7 times the amount of chlorotoluene. Suitable mineral acids used in the process of the invention include preferably hydrochloric acid, sulfuric acid, nitric acid and the like. Suitable alkyl chloroformates used in the second embodiment of the invention include alkyl esters having a straight chain or a branched chain and which have 1 to 4 carbon atoms such as methyl chloroformate, ethyl chloroformate, n-propyl chloroformate, is-propyl chloroformate, n-butyl chloroformate, iso-butyl chloroformate and the like. It is known from the prior art techniques that the reaction between chlorobenzene and sodium is very exothermic. However, in the present process, the reaction between chlorotoluene and sodium is not as exothermic and can be easily performed at low temperatures such as less than 30° C thus enabling ready control of the reaction temperature. As a result, no bitolyl by-product is formed by the side-reaction of tolyl sodium and chlorotoluene. In the process of the present invention, tolylsodium obtained by the reaction of chlorotoluene with sodium, can be heated in the reaction mixture without separation to effect rearrangement to benzyl sodium. Thus, it is unnecessary to react the product with a third component such as toluene as in the conventional process. Moreover, the formation of a by-product such as benzene does not occur from the presence of a third component in the reaction. The reaction steps of the present process are short in comparison to the steps of the known process of continuously producing phenylacetic acid, salts or alkyl esters thereof in high yield from chlorotoluene without separating and purifying the intermediate formed in each step. In the present process, even though a mixture of o-chlorotoluene and p-chlorotoluene is used as starting material, all of the starting materials can be converted to phenylacetic acid or an alkyl phenylacetate. Accordingly, a crude chlorotoluene produced by chlorinating toluene can be used as the starting material in the present process, and therefore, is a favorable industrial process.

EXAMPLE 1

Into a four necked flask equipped with a stirrer, a thermometer, a reflux condenser and a gas inlet, 50 ml of benzene was charged and 5.4 g of sodium was dispersed in the benzene. Thereafter 12.7 g of o-chlorotoluene was added dropwise to the dispersion over a period of 30 minutes. When o-chlorotoluene was added dropwise, an exothermic reaction resulted and the reaction temperature increased. However, the reaction temperature was controlled to 20° to 30° C by cooling the flask with water and o-chlorotoluene was added dropwise to the contents of the flask. After the addition of o-chlorotoluene, the reaction was continued at 30° C for 30 minutes with stirring. After the reaction of o-chlorotoluene with sodium, the reaction mixture was gradually heated to effect rearrangement at 80° C for 5 hours with stirring. After the reaction, the reaction mixture was cooled and carbon dioxide gas was introduced at a reaction temperature of 25° C to 28° C from the gas inlet at a rate of 0.8 to 1.0 liter/min. over 3 hours to effect reaction with the benzylsodium. After the reaction of carbon dioxide with benzylsodium, 50 g of methanol was added to the reaction mixture with stirring to inactivate the excess sodium and then, 50 ml of water was gradually added thereto. Thereafter, the reaction mixture was charged into a separatory funnel. The water phase was separated. The reaction mixture was further washed with 50 ml of water with shaking then the water phase was separated. The separated water phase was charged into a separatory funnel and was washed with 100 ml of 1N-HCl with shaking. Then, the product was extracted three times with 50 ml portions of ether. The extract was washed with water two times, and ether was removed by distillation under reduced pressure to concentrate the extract. The precipitated colorless plate-like crystals obtained had a fragrant smell and were separated by a filtration, whereby 12.7 g of phenylacetic acid having a melting point of 75° to 76° C (yield 93.4%) were obtained.

EXAMPLE 2

In accordance with the process of Example 1, 12.7 g of p-chlorotoluene were contacted and reacted with 5.4 g of sodium dispersed in 50 ml of cyclohexane at 20° C to 30° C and then the reaction mixture was heated to 80° C for 5 hours to rearrange the product. The reaction mixture was cooled to 20° C to 23° C and was gradually poured onto 10 g of solid carbon dioxide with stirring to effect the carbonylation reaction. After the reaction with carbon dioxide, the post-treatment procedure was conducted in accordance with the process of Example 1 to whereby 12.8 g of phenylacetic acid (yield 94.1%) were obtained.

EXAMPLE 3

In accordance with the process of Example 1, 12.7 g of chlorotoluene (a mixture of 67.03% of o-chlorotoluene and 32.97% of p-chlorotoluene) produced by reacting toluene with chlorine in carbon tetrachloride was mixed with 5.4 g of sodium dispersed in 50 ml of 1.4-dioxane. The reaction mixture was heated at 100° C for 3 hours to rearrange the product. The reaction mixture was cooled to 25° C to 28° C and carbon dioxide gas was introduced into the reaction mixture to effect carboxylation with the rearranged product. After the reaction, the post-treatment was carried out in accordance with the process of Example 1 whereby 13.1 g of phenylacetic acid (yield 96.3%) were obtained.

EXAMPLE 4

In accordance with the process of Example 1, 12.7 g of p-chlorotoluene was contacted with 5.4 g of sodium dispersed in 50 ml of dibutyl ether. The reaction mixture was heated at 110° C for 3 hours to effect rearrangement to the desired product.

The reaction mixture was cooled and 26 g of ethyl chloroformate were added dropwise to the reaction mixture at 18° C to 20° C with effect the carboxylation reaction.

After the reaction, the reaction mixture was washed sequentially with water, dilute hydrochloric acid, a 2% aqueous solution of sodium hydroxide and water. Then dibutyl ether was removed by distillation under reduced pressure and the product was distilled under reduced pressure whereby 11.8 g of ethyl phenylacetate having a boiling point of 100.5° C/10 mmHg (yield 71.9%) were obtained.

EXAMPLE 5

In accordance with the process of Example 1, 12.7 g of chlorotoluene (a mixture of 67.03% of o-chlorotoluene and 32.97% of p-chlorotoluene) which was produced by reacting toluene with chlorine in carbon tetrachloride, was mixed with 5.4 g of sodium dispersed in 50 ml of 1,4-dioxane and rearrangement was accomplished by heating the mixture at 100° C for 3 hours.

In accordance with the process of Example 4, the reaction mixture was cooled and 26 g of ethyl chloroformate was added dropwise to the reaction mixture at 18° to 20° C with stirring and the product was post-treated whereby 10.9 g of ethyl phenylacetate (yield 66.5%) were obtained.

EXAMPLES 6 TO 8

In accordance with the process of Example 4, chlorotoluene was mixed and reacted with sodium dispersed in the inert organic solvent shown in Table 1. The reaction mixture was heated to effect rearrangement to the product and the alkyl chloroformate shown in the table were reacted with the rearranged product, whereby the following alkyl phenylacetate phenylacetates were obtained. The results also shown in Table 1.

Table 1

| Example | 6 | 7 | 8 |
|---|---|---|---|
| Chlorotoluene | Cl—⟨⟩—CH$_3$ | Cl on ring with CH$_3$ 67.3%; Cl—⟨⟩—CH$_3$ 32.97% | Cl on ring with CH$_3$ 67.03%; Cl—⟨⟩—CH$_3$ 32.97% |
| Solvent | benzene | 1,4-dioxane | 1,4-dioxane |
| Reaction temperature of reaction rearrangement | 80° C (5 hr) | 100° C (3 hr) | 100° C (3 hr) |
| Alkyl chloroformate | ClCOOCH$_3$ | ClCOOC$_3$H$_7$ | ClCOOCH$_2$CH(CH$_3$)$_2$ |
| Product alkyl phenylacetate | ⟨⟩—CH$_2$CO$_2$CH$_3$ methyl phenylacetate b.p.131–133° C/50 mmHg yield 69.8% | ⟨⟩—CH$_2$CO$_2$C$_3$H$_7$ n-propyl phenylacetate b.p.126° C/20 mmHg yield 67.7% | ⟨⟩—CH$_2$CO$_2$CH(CH$_3$)$_2$ iso-butyl phenylacetate b.p.136° C/20 mmHg yield 61.9% |

What is claimed is:

1. A process for producing benzylsodium or chlorobenzylsodium which comprises:
preparing tolylsodium or chlorotolylsodium by reacting chlorotoluene or dichlorotoluene with a dispersion of sodium in an inert organic solvent at a temperature of 0° C to 50° C; and rearranging said tolylsodium or chlorotolylsodium at a temperature in the range of 40° C to 150° C to said benzylsodium or chlorobenzylsodium.

2. The process of claim 1, wherein said inert organic solvent is n-hexane, isohexane, heptane, cyclohexane, petroleum ether, ligroin, benzene, isopropyl ether, butyl ether, tetrahydrofuran or dioxane.

3. The process of claim 1, wherein dichlorotoluene is reacted with sodium and the product obtained with this reactant is chlorotolylsodium which is then rearranged to chlorobenzylsodium.

4. The process of claim 1, wherein the reaction of chlorotoluene with sodium is conducted at 10° C to 40° C and the rearrangement is conducted at 50° C to 120° C.

5. In a process for producing phenylacetic acid, salt or esters thereof by preparing benzylsodium or chlorobenzylsodium and reacting said benzylsodium or chlorobenzylsodium with a carboxylating agent, the improvement which comprises:
  preparing tolylsodium or chlorotolylsodium by reacting chlorotoluene or dichlorotoluene with a dispersion of sodium in an inert organic solvent at a temperature of 0° C to 50° C; and rearranging the tolylsodium or chlorotolylsodium at a temperature in the range of 40° C to 150° C to said benzylsodium or chlorobenzylsodium.

6. The process of claim 5, wherein said carboxylation is performed to produce sodium phenylacetate by reacting carbon dioxide with benzyl sodium and then phenylacetic acid is prepared by reacting said sodium phenylacetate with a mineral acid.

7. The process of claim 5 wherein an alkyl phenylacetate is prepared by reacting an alkyl chloroformate with said benzyl sodium.

8. The process of claim 7, wherein said alkyl chloroformate is methyl chloroformate, ethyl chloroformate, n-propyl chloroformate, iso-propyl chloroformate, n-butyl chloroformate or iso-butyl chloroformate.

9. The process of claim 5, wherein dichlorotoluene is reacted with sodium and the obtained product is chlorotolylsodium which is rearranged to chlorobenzylsodium and then said chlorobenzylsodium is converted to said chlorophenylacetic acid, salt or ester.

10. The process of claim 5, wherein said tolylsodium is formed by adding chlorotoluene to a dispersion of sodium in an inert solvent at 0° C and then the reaction mixture is heated at 50° C to 120° C to rearrange said tolyl sodium to benzyl sodium.

11. The process of claim 5, wherein said carboxylating agent is carbon dioxide gas or solid carbon dioxide.

12. The process of claim 5, wherein said chlorotoluene starting material is a mixed chlorotoluene produced by chlorinating toluene.